(12) United States Patent
Bremner et al.

(10) Patent No.: US 6,692,632 B1
(45) Date of Patent: Feb. 17, 2004

(54) METHOD OF PRODUCING HYDROXYL RADICALS FOR CHEMICAL REACTIONS

(75) Inventors: David Bremner, Dundee (GB); Arthur Ernest Burgess, Glasgow (GB)

(73) Assignee: University of Abertay Dundee, Dundee (GB)

( * ) Notice: Subject to any disclaimer, the term of this patent is extended or adjusted under 35 U.S.C. 154(b) by 0 days.

(21) Appl. No.: 10/069,939

(22) PCT Filed: Sep. 1, 2000

(86) PCT No.: PCT/GB00/03344
§ 371 (c)(1),
(2), (4) Date: Jun. 25, 2002

(87) PCT Pub. No.: WO01/16031
PCT Pub. Date: Mar. 8, 2001

(30) Foreign Application Priority Data

Sep. 1, 1999 (GB) .............................................. 9920532

(51) Int. Cl.[7] .............................. C25B 3/00; C25B 1/00
(52) U.S. Cl. ........................................ 205/413; 205/464
(58) Field of Search ..................... 204/157.15; 205/413, 205/464

(56) References Cited

U.S. PATENT DOCUMENTS

| | | | |
|---|---|---|---|
| 4,676,878 A | 6/1987 | Chez | 204/101 |
| 4,925,540 A | 5/1990 | Dhooge | 204/157.42 |
| 5,707,508 A | 1/1998 | Surma et al. | 205/688 |
| 6,139,755 A | 10/2000 | Marte et al. | 210/752 |

FOREIGN PATENT DOCUMENTS

| | | |
|---|---|---|
| CH | 605 421 A | 9/1978 |
| DE | 34 28 582 A | 3/1985 |
| DE | 196 18 074 A | 9/1997 |
| DE | 196 18 074 A1 * | 9/1997 |
| DE | 197 00 164 A1 | 7/1998 |
| EP | 0694501 A | 1/1996 |
| EP | 1 008 556 A2 | 6/2000 |
| JP | 62-74485 | 4/1987 |
| JP | 8-89975 | 4/1996 |
| WO | WO 96 32175 A | 10/1996 |
| WO | WO 97 28294 A | 8/1997 |
| WO | WO 98 17589 A | 4/1998 |
| WO | WO 99 01382 A | 1/1999 |
| WO | WO 00 17113 A | 3/2000 |
| WO | WO 00 34184 A | 6/2000 |

OTHER PUBLICATIONS

Tomat et al., "Electrocatalytic Production of OH Radicals and Their Oxidative Addition to Benzene", J. of Applied Electrochemistry, vol. 1 (month unavailable, 1971), pp. 185–188.*

Li, "Multi–Hyphenated Energy Systems in Synthesis and Environmental Cleanup", Jan. 1998, pp. 1–2.*

* cited by examiner

Primary Examiner—Edna Wong
(74) Attorney, Agent, or Firm—Drinker Biddle & Reath LLP

(57) ABSTRACT

A method of reacting chemicals comprising the exposure of the reactants to ultrasound and electrochemical energies in the presence of a metal or metal salt and hydrogen peroxide. HO* radicals are efficiently formed and react with a carbon-based reactant to form a carbon radical which then reacts with other reactants or may dimerize. The invention regenerates the metal ions and may be performed using no special facilities. Increased product yield was achieved for a number of hydroxylation reactions.

19 Claims, 5 Drawing Sheets

METHOD OF PRODUCING HYDROXYL RADICALS FOR CHEMICAL REACTIONS

This Application is the U.S. National Phase Application of PCT International Application No PCT/GB00/03344 filed Sep. 1, 2000.

This invention relates to a method of reacting chemicals. In one embodiment it relates to a method of driving chemical synthesis of small molecules such as chemical intermediates, but can be used to drive destruction of others such as pollutants.

DESCRIPTION OF THE RELATED ART

Hydroxyl radicals HO* are useful in the polymerisation of a variety of commercial polymers, oxidative synthesis of various organic compounds and destruction of water pollutants [1–3]. In some of these reactions such as polymerisation via a chain reaction mechanism, hydroxyl radicals act as an initiator and the amount required is fairly small. In other reactions, such as the synthesis of phenol via direct hydroxylation of benzene, hydroxyl radicals are consumed as a reagent in large quantities. There are also cases in which HO* consumption is not only in large quantities but also at high concentrations. An important example is the dimerization of pivalic acid in the synthesis of tetramethyladipic acid [4,5]. The key reaction step is the dimerization of two radicals of the substrate produced through hydrogen atom abstraction by HO*. In order for such a bimolecular radical-radical reaction to proceed at a rate which is sufficient for synthetic purposes, HO* must be present at a relatively high concentration. This presents difficulties owing to the relatively slow kinetics of the chemical reactions utilised. Hydroxyl radicals react readily with a variety of compounds often at a rate close to diffusion control (the rate constants of hydrogen abstraction and electrophilic substitution reactions, for example, are in the range $10^8$–$10^{10}$ $M^{-1}s^{-1}$) [6–8]. If the reaction conditions are too intense, the radicals generated tend to react indiscriminately and the reaction becomes uncontrollable. Therefore, there is a need for developing a catalytic scheme in which radicals such as HO* can be generated efficiently under relatively mild conditions so as to allow better control of the reaction.

SUMMARY OF THE INVENTION

The invention provides a method of reacting chemicals, the method comprising:
  exposing at least one metal electrode to one or more different energies from the group comprising:
    ultrasonic energy, electrochemical energy, electrical energy, thermal energy, and visible and invisible radiation;
    generating hydroxyl radicals from any suitable source; and
    reacting the hydroxyl radicals with one or more reactants.

Preferably the metal electrode is exposed to electrochemical energy.

Preferably the metal electrode is also exposed to ultrasound energy. Preferably a cup-horn apparatus is used to apply the ultrasound energy.

In one embodiment the present invention provides a method of reacting chemicals, the method comprising:
  exposing the metal electrodes to electrochemical energy;
  generating hydroxyl radicals; and
  reacting the hydroxyl radicals with one or more reactants.

Exposure to the electrochemical and ultrasound energies is preferably conducted under controlled conditions.

Preferably there are two electrodes. Preferably the electrodes comprise iron but may comprise any one or a combination of two or more metals chosen from iron, cobalt, copper, cerium, nickel, stainless steel, manganese, vanadium, molybdenum, titanium, platinum, iridium, osmium, ruthenium, gold and silver.

Optionally a first electrode comprises $Fe^{2+}/Fe^{3+}$ in conjunction with $Ce^{3+}/Ce^{4+}$ and a second electrode comprises a noble metal electrode, and the following reaction takes place at the first electrode:

This process can form part of the recycling of iron ions when $Fe^{2+}$ is consumed in a Fenton-like reaction forming $Fe^{3+}$ and $HO^-$.

The method may be used to decompose chemicals such as in the destruction of pollutants etc or alternatively the method may be used in the synthesis of chemicals.

In a preferred embodiment the present invention provides a method of chemically synthesising a reaction product from reactants, said method comprising the following steps:
  a) electrochemically forming $Fe^{2+}$ ions;
  b) exposing said $Fe^{2+}$ ions to $H_2O_2$ to produce HO*;
  c) exposing said HO* to the reactants in conditions suitable for said HO* and said reactants to chemically react together to promote formation of said reaction product.

Preferably the reaction mixture of any of steps a), b) and/or c) is also exposed to ultrasonic radiation.

The reactants are preferably heated, and can be exposed to ultrasonic and electrochemical energy at the same time or consecutively, optionally at an given temperature. Where the reactants are exposed to ultrasound and electrochemical energy consecutively they are preferably first exposed to electrochemical energy.

$Fe^{2+}$ ions are preferably generated through electrochemical dissolution of an iron anode in electrolytes of eg acetonitrile-water mixtures. In this way, the rate of $Fe^{2+}$ generation can be controlled conveniently by adjusting the electrode potential, current, or the composition of the electrolyte. The pristine ion $Fe^{2+}$ produced reacts instantly with the substrate (eg $H_2O_2$) before reaching salvation equilibrium and therefore is more potent than that delivered traditionally via the addition of a ferrous salt solution prepared in advance, in which the iron (II) ions are completely solvated in water, aqueous acid or acetonitrile-aqueous acid mixtures.

The method preferably involves generating hydroxyl radicals in a Fenton-like process ($Fe^{2+}+H_2O_2 \rightarrow HO^*+HO^-+Fe^{3+}$) [9]. The generated radical can be utilised in a hydroxylation reaction, and typically in an oxidative hydroxylation reaction.

The Fenton process is attractive in that the reagents used are inexpensive, and no special facilities such as an electron accelerator (used in pulse radiolysis) are required [9].

Alternatively the method may comprise generating the hydroxyl radicals by reacting the metal with hydrogen peroxide by the following equation:

wherein M is Fe or another metal and n is any value from 1 to 7.

It is important that the reaction produces a hydroxyl radical as part of the process, but otherwise parameters can be varied.

The invention preferably involves the use of catalytic schemes [10], electrochemical regeneration [11] of $M^{n+}$, (for example Fe+2Fe$^{3+}$→3Fe$^{2+}$) with or without the synergistic coupling of ultrasonic energy and the optional use of an unreactive solvent such as acetonitrile [10] in order to ameliorate the need for constant addition and consumption (rather than recycling) of ferrous salts, limited control of the reaction due to simple use of chemical and thermal energies alone and the need for an aqueous medium in which the solubility of most organic substrates is often too low.

The free hydroxyl radical preferably reacts with a carbon based reactant to remove a hydrogen atom and generate a carbon-based radical as a result. The carbon-based radical can then dimerize or react with other carbon-based radicals or other reactants.

The method is preferably used in synthesis, but can also be useful in the destruction of pollutants etc. In certain embodiments of this nature, the use of external current applied to the system is not necessary, and a simple galvanic cell can be set up.

BRIEF DESCRIPTION OF THE FIGURES

Embodiments of the invention will now be described by way of illustration with reference to the following figures wherein.

DETAILED DESCRIPTION OF THE INVENTION

Tagawa et al [10] describes a method to chemically synthesise phenol. There, the supported catalyst of ferrous chloride was Drepared by soaking up an aqueous solution of FeCl$_2$ (1 mmol in ca. 10 ml) in 20 g silica gel and drying the gel at 100° C. for 2 h. The gel (4 g, 0.2 mmol Fe$^{2+}$) and benzene (15 ml, 170 mmol) were added to acetonitrile (58 ml, 1.1 mol), and reaction was initiated by addition of H$_2$O$_2$ (5.5 ml, 30% by weight, 55 mmol) with the mixture being maintained at 35(±5)° C. and stirred (at ca. 200 rpm) using a magnetic stirrer.

Embodiments of the present invention generate Fe$^{2+}$ electrochemically in a one-compartment glass cell. Here, iron foil of 99% purity and 0.25 mm thickness was used as the cathode and anode, and a saturated calomel electrode (SCE) as the reference electrode. The electrolyte solution was acetonitrile, containing 0.1 M LiClO$_4$ and the required amounts of benzene (0.42–0.93 M), hydrogen peroxide (0.97 M), H$_2$SO$_4$ (0.017–0.1 M), and in some cases a certain amount (20 ml) of distilled water. A computer-controlled μAutolab potentiostat was used for electrochemical control.

The ultrasound (US) source was a Sonics and Materials Model VC600 operating at 20 kHz. The output can be continuous or pulsed with varying percentage of cycle duty from 10 to 100% (i.e. continuous). Two methods, a probe and cup-horn bath, were used for ultrasonic irradiation. The full power (600 W electrical and 100 W ultrasonic) of the ultrasound generator can be attenuated in 10 levels.

The phenol synthesised was analysed using a Perkin-Elmer 8310 gas chromatograph under selected conditions with 2,4-dimethylchlorobenzene used as the internal standard. All chemicals were of AnalaR grade and were used as received. Wall-coated fused silica capillary columns with a CP-WAX-52CB or a CP-OV-1 coating were used in conjunction with nitrogen carrier gas and a flame ionisation detector. Identification of the components in the reaction mixture was made by comparing the retention times with the known pure components, and their variation with temperature programs. Quantification of phenol concentration was carried out through both external and internal standards with a margin of error <5%. The amount of phenol synthesised was obtained through the total volume of the reaction mixture and the concentration of the GC analysis. The overall margin of error of the yield data is estimated to be between 0.5 (for yields less than 10%) and 1.0% (for yields greater than 10%). For the purpose of qualitative identification, GC peaks of unreacted benzene can be separated partially from the solvent acetonitrile by using a low initial temperature of 30° C. and relatively slow scanning of column temperature (<10° C./min). Benzene is eluted before acetonitrile on the more polar CP-WAX-52CB coating and after acetonitrile on the less polar CP-OV-1 coating. (For phenol, the CP-WAX-52CB coating provides larger sample capacity and better peak symmetry than the CP-OV-1 coating, but both produce the same quantification within the margin of error.)

Tetramethyladipic acid was prepared from pivalic acid using electrochemical generation of hydroxyl radicals in the presence of ultrasound as follows.

Pivalic acid (25 g, 0.245 mole), water (500 mL), 6M sulphuric acid (45 mL), 2M hydrochloric acid (10 mL) and 30% hydrogen peroxide (25 mL, 0.22 mole) were stirred with an overhead stirrer (ca 250 rpm) in a 1L beaker. The reaction vessel was immersed in a cup horn sonicator and irradiated at ultrasound level 8 and 50% pulse rate. Iron electrodes (80 cm2) were connected to a direct current converter and 1A current was passed into the reaction mixture for 250 minutes at a temperature of 24° C.

After this time the reaction mixture was transferred to a 2L round bottomed flask fitted for steam distillation and 1 L of water/pivalic acid mixture was distilled off. The residue was extracted with ethyl acetate (2×250 mL), the combined organic fractions dried (MgSO$_4$) and solvent removed in vacuo to yield 8.3 g of a brown solid. Recrystallisation from methanol gave TMAA (8 g; 32%) as a white crystalline solid.

Results

EXAMPLE 1

Chemical synthesis of phenol using supported catalysts was first conducted at 30° C. using the literature method [10] to provide baseline results. The reaction mixture was stirred with a magnetic stirrer at ca. 200 rpm. As the reaction proceeded, the colour of the mixture changed from colourless to light yellow, then orange. After reaction for 30, 90 and 120 min, phenol yields were 1.1, 1.8 and 2.2%, which are close to those reported previously [10]. The continued increase in phenol yield with reaction time shows that phenol concentration in the reaction mixture is well below the concentration allowed by the side reactions, such as phenol destruction through oxidation by the HO*. If the reaction is allowed to proceed at ca. 70° C. by refluxing the solution, the above-mentioned colour changes are accelerated and further changes to brown and black follow. Accompanying the blackening of the solution, extensive bubbling and foaming occurred which ceased only when $H_2O_2$ was consumed as shown by the starch-iodide test. At the end of the reaction (lasting 10 to 15 min), a higher phenol yield of 10% was achieved, but the reaction was evidently out of control and the reactant $H_2O_2$ was destroyed by thermal catalytic decomposition.

EXAMPLE 2

Phenol yield was improved by ultrasound radiation (US) to varying degrees, depending upon the input mode, power and other conditions.

Figure 3:
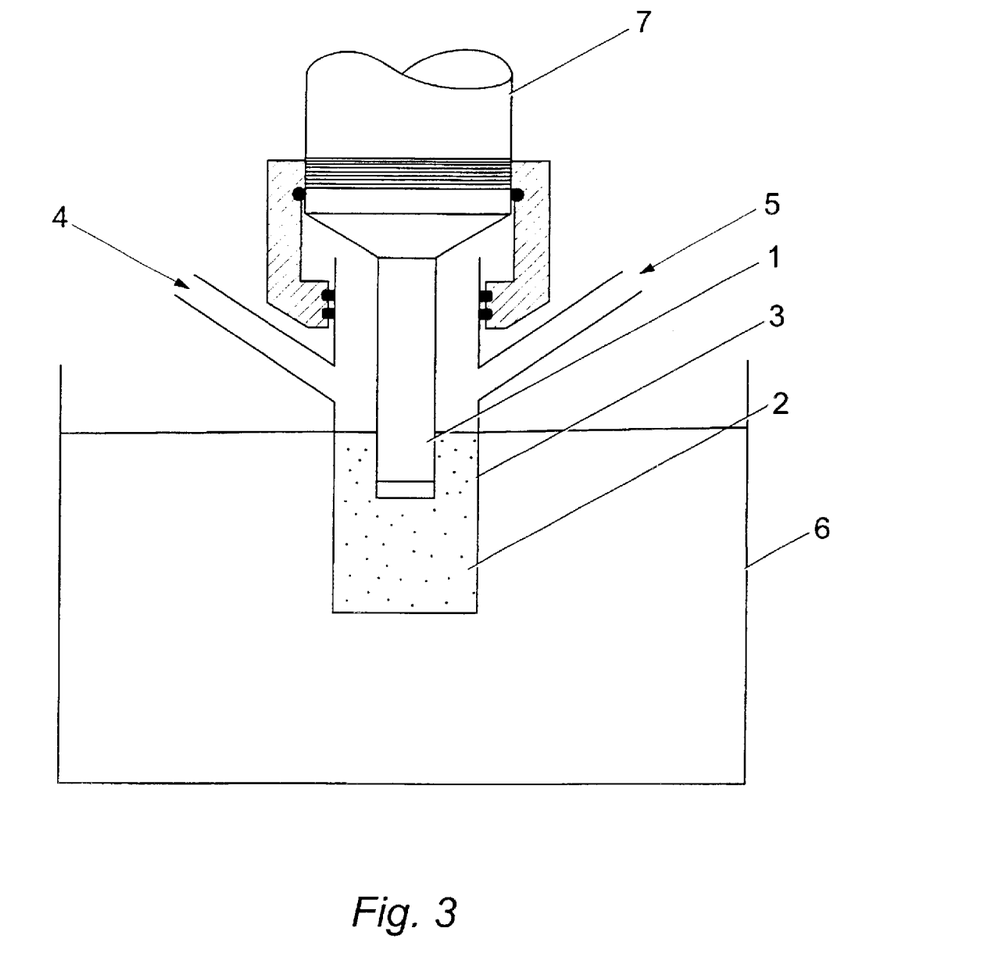

Table 1 lists the yields of phenol achieved using the immersed sonic probe shown in FIG. 3. The probe 1 was immersed directly into the sample 2 contained in a reaction vessel 3. The experiments were optionally performed in an inert atmosphere and so gas inlets 4 and outlets 5 were provided. A cooling bath 6 normally surrounded the reaction vessel 3 as the application of ultrasound typically resulted in an increased temperature. A titanium horn 7 produced the ultrasound energy which was directed into the sample 2 via the probe 1.

At a reaction temperature of 35° C. (entry 1 of Table 1), phenol yield after 30 min reaction was double that achieved under the same conditions without US input. This shows clearly the positive effect of US on the synthesis. An increase in US input power from level 3 (entry 1) to level 5 (entry 2), however, did not result in a higher yield.

The yield at 30 min reaction in entry 1 is 38% higher than that in entry 3 achieved at a lower reaction temperature 0–5° C. (maintained by an ice bath), showing that an increase in reaction temperature favours phenol yield.

EXAMPLE 3

Figure 4:
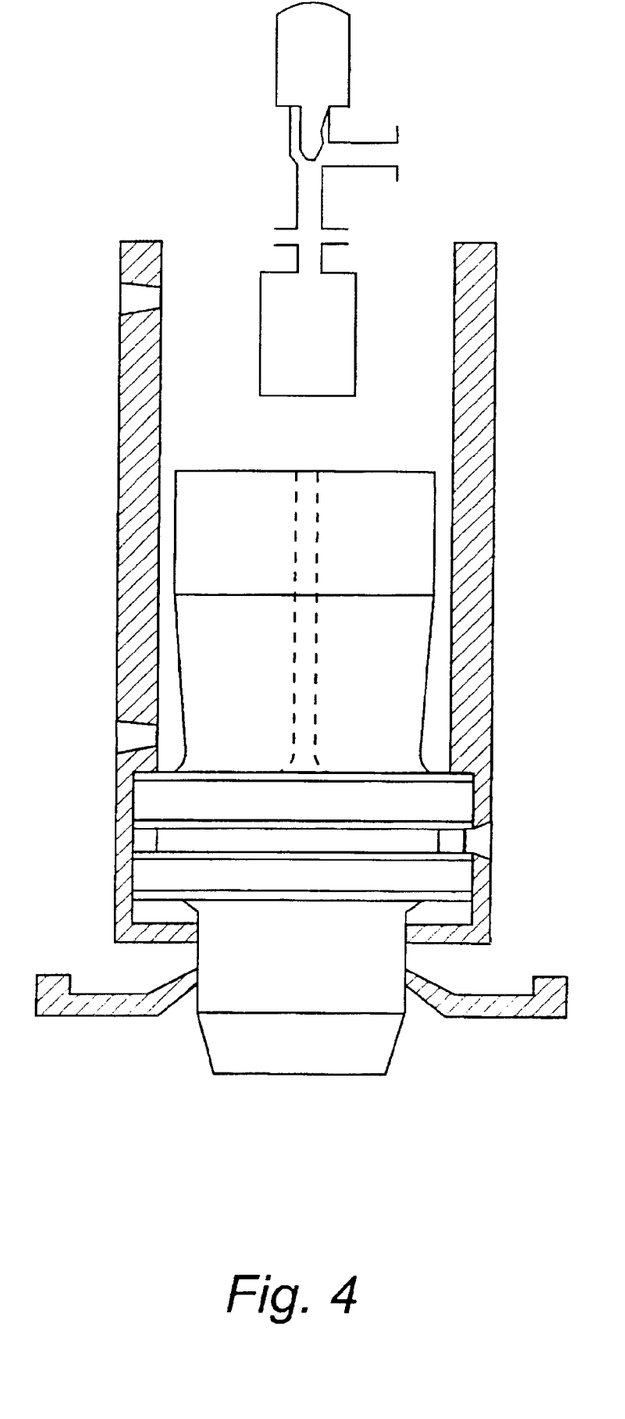
FIG. 4 is a cup-horn apparatus used to apply ultrasonic energy.

Table 2 shows phenol yields achieved under various conditions using the ultrasonic cup-horn bath. A standard configuration of an ultrasonic cup-horn bath is shown in FIG. 4.

Figure 5:
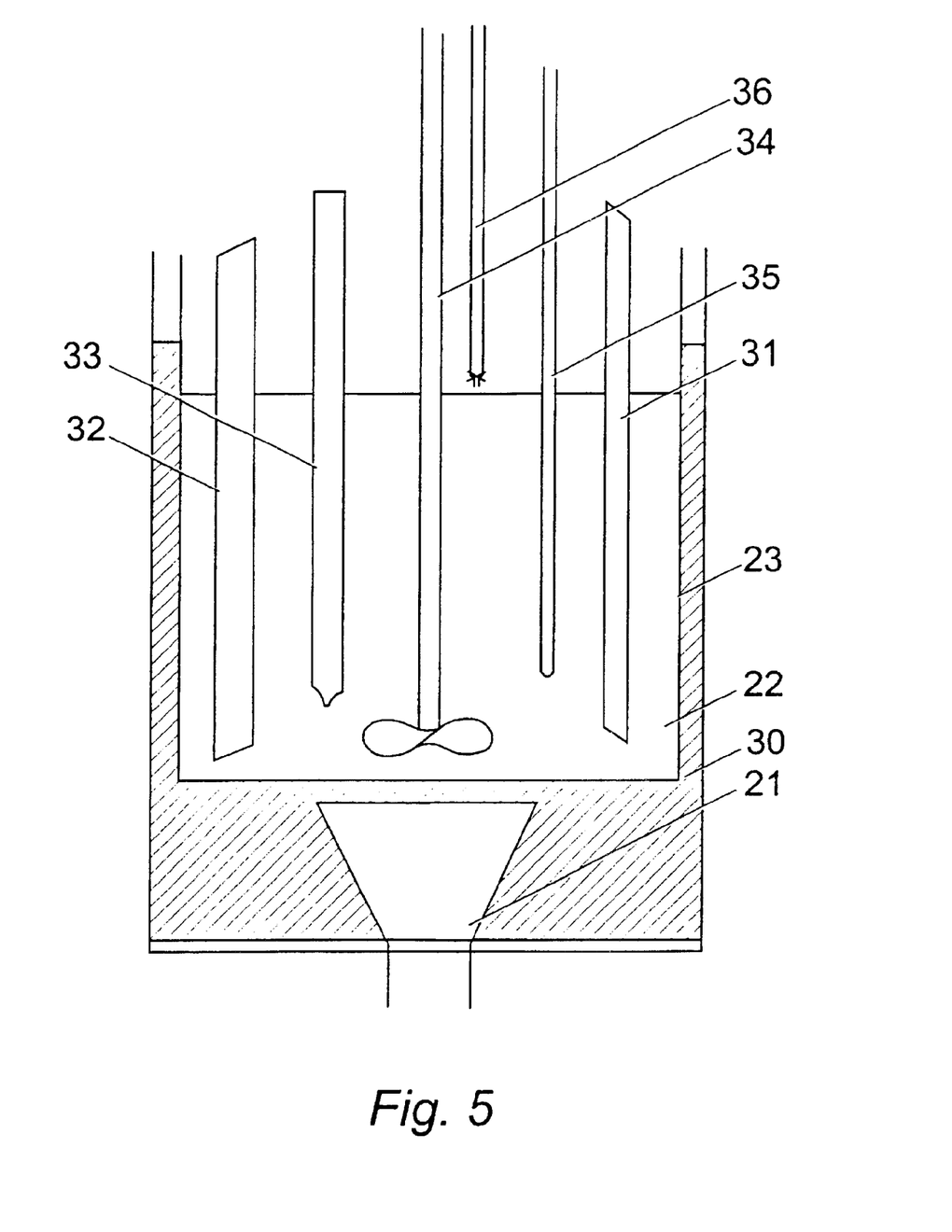
FIG. 5 is an alternative cup-horn apparatus used to apply ultrasonic and electrochemical energy.

FIG. 5 shows a cup-horn bath used in this example. A reaction vessel 23 was immersed into a water bath 30. Iron electrodes 31, 32 were inserted into the reaction mixture 22. A reference electrode 33, stirrer 34, and temperature probe 35 were normally inserted into the reaction mixture 22. The $H_2O_2$ is normally added via the burette 36.

Comparison between entry 2 in Table 2 and entry 2 in Table 1 shows that the bath is more effective than the probe: the yield increased from 2.3% to 6.2% after 60 min reaction even under a reduced radiation duration (50% as opposed to 100%). Using the same US bath and at the same power level (level 5), the yield is increased significantly by extension of radiation time from 20 to 50% of cycle duty (entries 1 and 2 of Table 2). A simultaneous increase in US power and hydrogen peroxide concentration (entry 3 compared with entry 2) leads to a marked increase in phenol yield to over 12% after 30 min reaction. An increase in both reaction temperature and hydrogen peroxide excess (entry 6 compared with entry 3) resulted in a further significant increase in the yield to over 15% and shortening of reaction time from 30 to 10 min. The effect of hydrogen peroxide excess (relative to benzene) can be seen clearly by comparing entry 3 with entry 5. An increase in the excess from 25% to 100% leads to an increase in the yield at 30 min reaction by 36% even at an unfavourable lower reaction temperature. These results show that phenol yield is favoured by an increase (within a certain limit) in ultrasonic radiation (power level and duration), reaction temperature and hydrogen peroxide excess. Therefore, at low levels of these parameters, the yield increases consistently with reaction time (entries 1 and 2), whereas at high levels, it reaches a plateau (entry 3) or maximum at an accelerated speed and begins to decline (entries 5 and 6) owing to undesirable side reactions of the product.

The mechanism of benzene hydroxylation involves a cyclohexadienyl radical intermediate (reaction 1) [9]. Oxidation of the intermediate by $Fe^{3+}$ ions produces phenol and at the same time returns the iron catalyst to its divalent state for the next round use:

(1)

(2)

Alternatively, the cyclohexadienyl radical intermediate can react with $H^+$ and collapse back to benzene:

(3)

Consistent with this mechanism, acidification of the reaction solution reduces phenol yield drastically. With 6 mmol $H_2SO_4$ added, the solution (ca.72 ml) remained clear (an indication of absence of phenol synthesis) throughout and after 60 min of reaction, phenol yield is essentially zero (entry 4 in Table 2), owing to significant acceleration of reaction 3.

EXAMPLE 4

In order to establish the appropriate conditions for $Fe^{2+}$ generation using the iron electrode, we studied the dissolution and passivation features of metallic iron in acetonitrile-water mixtures in comparison with neat solvents. Such mixtures are created when an aqueous solution of hydrogen peroxide is added to acetonitrile to initiate the reaction. Experiments showed that in acetonitrile without added water, the passive oxide film on iron formed during air exposure is maintained over a wide potential range (up to 0.5 V) and active dissolution (predominantly in the form of $Fe^{2+}$) is absent. Iron dissolution occurs in the transpassive region more positive than 1.2 V (most likely in the form of $Fe^{3+}$ which is not directly useful for the synthesis). Active dissolution, however, can be effected by addition of a small proportion of water.

Figure 1A:
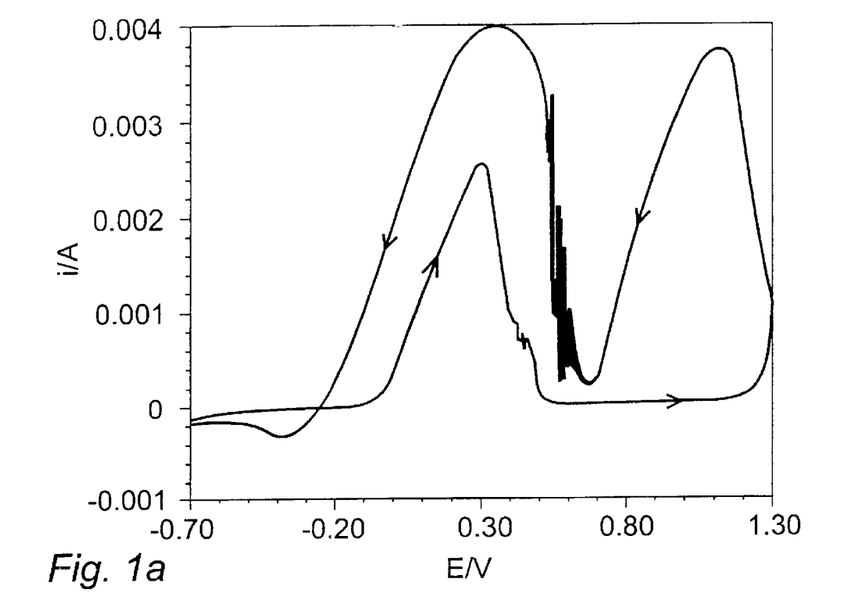
FIG. 1a is a cyclic voltammogram diagram showing the dissolution and passivation features of iron in acetonitrile-water mixtures.
Figure 1B:
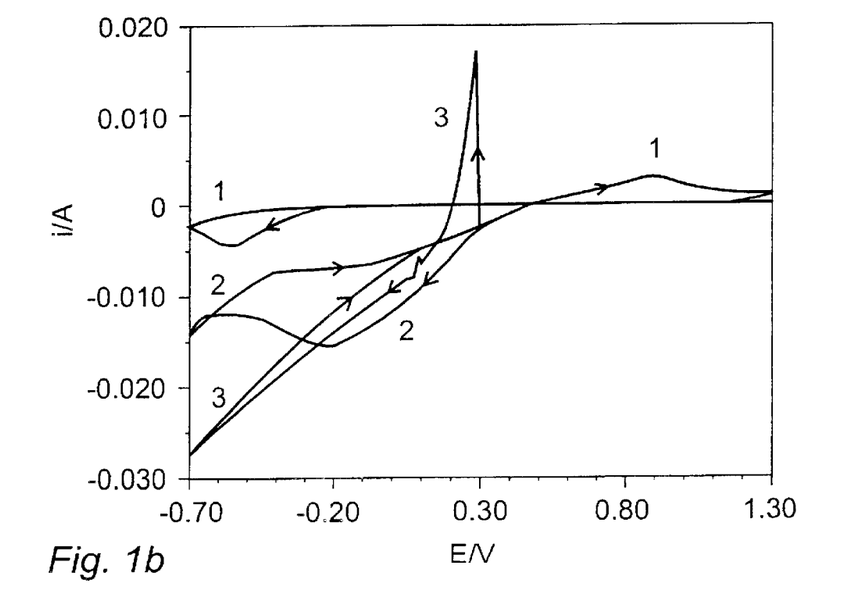
FIG. 1b is a cyclic voltammograms showing the effects of solution acidity on the dissolution and passivation behaviour of iron in the presence of hydrogen peroxide.

FIG. 1a shows a cyclic voltammogram showing the dissolution and passivation features of iron in acetonitrile-water mixtures. The electrolyte was an acetonitrile-6% $H_2O$ (v/v) mixture containing 0.2 M $LiClO_4$. FIG. 1b shows cyclic voltammograms showing the effects of solution acidity on the dissolution and passivation behaviour of iron in the presence of hydrogen peroxide. The electrolyte was an acetonitrile-10% $H_2O$ mixture containing 0.2 M $LiClO_4$, 0.848 M $H_2O_2$ and 0 M (curve 1), 0.018 M (curve 2) and 0.108 M $H_2SO_4$ (curve 3), respectively. The potential sweep rate was 20 mV/s for all.

Compared with those in neat acetonitrile and water, the overall features of the FIG. 1 CVs are a mixture of those in the two component acetonitrile-water solvents. Active dissolution is observed between—0.3 and 0.5 V and passivation between 0.5 and 1.1 V. The features of these two processes are more similar to those in water. Transpassive dissolution during the anodic scan starts from a lower potential of 1.1 V compared with water and is more similar to acetonitrile.

FIG. 1b shows the effects of addition of hydrogen peroxide into neutral (curve 1) and acidic (curve 2) acetonitrile solutions containing 2% water. Hydrogen peroxide oxidises the iron surface to produce a protective layer of iron oxide and thus acts as a passivator. In the neutral solution, passivation dominates and iron behaves as an inert electrode. (The anodic peak between 0.4 and 1.3 V and the cathodic peak between—0.2 and—0.7 V result from oxidation and reduction of hydrogen peroxide). If the acidity of the solution is increased, however, active dissolution is favoured and passivation becomes more difficult, as shown by curve 3 in FIG. 1b. A large anodic peak (17.5 mA) at 0.29 V with an extremely sharp rising edge (on the right) was observed during the cathodic (not anodic) scan, resulting from enhanced active dissolution due to the increased acidity. At this potential the passive film was suddenly broken down and iron dissolution occurred essentially over the whole electrode surface. The formation of a new passive film by hydrogen peroxide results in the decrease in the anodic current (the tail of the peak) eventually to cathodic values due to $H_2O_2$ reduction.

The electrochemistry shows that active dissolution of iron is suppressed by acetonitrile (in comparison with water) and hydrogen peroxide, but facilitated by an increase in acidity and water content. By adjusting the concentration of these components and the electrode potential (or current density), the speed of iron dissolution in the form of $Fe^{2+}$ can be tuned to suit the need of phenol synthesis under particular conditions. The presence of benzene during phenol synthesis does not alter the electrochemistry significantly because it is not electroactive in the potential range of interest. (The effects from possible adsorption and changes in dielectric properties of the solvents are relatively minor.)

Figure 2:
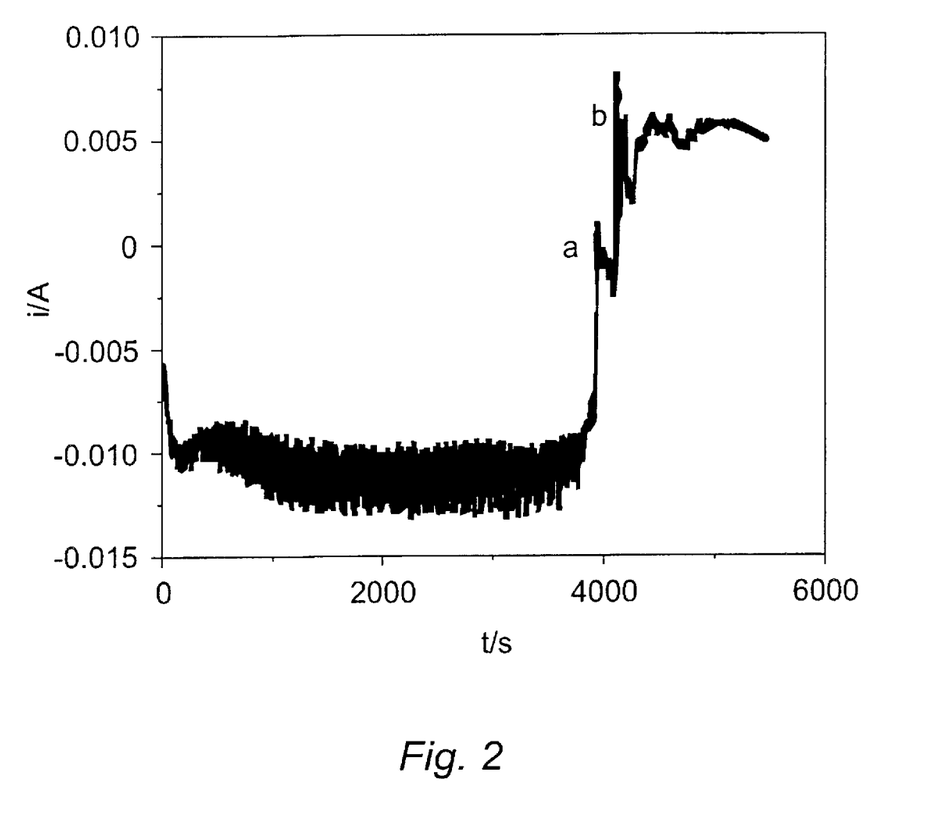
FIG. 2 is a current-time curve recorded during the electrochemical synthesis of phenol using acetonitrile as the reaction medium to solubilize the reactant benzene; and, FIG. 3 is an immersed probe apparatus used to apply ultrasonic energy.

FIG. 2 shows a current-time curve recorded during the electrochemical synthesis of phenol using acetonitrile as the reaction medium to solubilize the reactant benzene. The iron working electrode was held at a constant potential of 0.3 V vs SCE. The reaction medium consisted of acetonitrile (50 ml), 1 M sulphuric acid (1 ml), 30% wt hydrogen peroxide (5 ml) and benzene (15 ml).

The potential was set at a constant value of 0.3 V in the active dissolution region. After the initial increase in the cathodic direction during the first 120 s, the current stabilised at about −11 mA in the subsequent 3480 s. The scattering of current is due partly to stirring, but mainly to interactions between the opposing processes of dissolution and passivation. As the electrolysis proceeds, part of the electrode surface became covered with brown coloured patches characteristic of iron rust, indicating dissolution of metallic iron (generation of $Fe^2$ and subsequent oxidation). After 60 min reaction, stirring was stopped for sample collection. At this point, the current spontaneously decreased significantly and turned anodic briefly (peak a) before returning to a small cathodic value between 1 and 3 mA in the subsequent 2 min. In order to compare the effects of current polarity, the iron rust and organic mass attached to the electrode surface were scraped off with a spatula to promote active dissolution. Following the cleaning, the current turned anodic (peak b) and stabilised subsequently at ca. 5 mA. When the reaction was stopped after 90 min, the solution was light-orange coloured and a significant amount of hydrogen peroxide remained.

GC analysis shows that the predominant product of the electrochemical synthesis is phenol, the total content of by-products being small. The amount of phenol synthesised during the first 60 min was only 20% of that after 90 min reaction. In other words, the rate of phenol synthesis during the last 30 min of reaction under an anodic current is 7 fold faster than that during the first 60 min under a cathodic current. Therefore, generation of hydroxyl free radicals, and hence production of phenol, is facilitated by the dissolution of metallic iron.

Table 3 gives phenol yield achieved by electrochemical synthesis under an anodic current. While facilitating iron dissolution which favours phenol synthesis, an increase in the acidity (6 mmol $H_2SO_4$) of the electrolyte (entry 2 compared with entry 1) drives the cyclohexadienyl radical back to benzene, which reduces the yield. Under the reaction conditions, the latter process dominates and phenol yield decreases with increasing acidity from 9.0% at 110 min reaction to 2.8 % at 180 min reaction. The observation is consistent with that of chemical synthesis using supported catalysts. Chloride is well known to facilitate iron dissolution owing to its prominent polarizability among other properties. Therefore, addition of a small amount of HCl (0.5 mmol) to the solution shortened reaction time and increased phenol yield considerably (entry 3 compared with entry 2). A similar effect is observed for water, i.e. an increase in water content in the reaction mixture accelerates the synthesis and enhances the yield (entry 4), owing to facilitated generation of $Fe^{2+}$ through iron dissolution. A yield of 13% is reached with electrochemical synthesis, which is about the same as that achieved at a similar reaction temperature with the 'supported catalyst+US radiation' scheme as discussed above in examples 2 and 3.

One problem with the electrochemical approach is the destruction of phenol at late stages of synthesis which limits further enhancement of the yield. When the concentration of phenol reaches a certain level, fast blackening of the solution occurs similar to the situation with pure chemical synthesis at reflux temperature. Accompanying the blackening, the temperature rises quickly and a precipitate is often produced, indicating exothermal side reactions which are more favourable energetically than the hydroxylation of benzene. Further oxidation of phenol may follow the hydroquinone and quinone path:

(4)

The quinone produced may be further degraded oxidatively to low-molecular-weight products and eventually to $CO_2$ [3,15,16,27] or may condense to form polymers [27]. The latter process appears particularly significant in an aqueous solution free from or relatively low in acetonitrile when $Fe^{2+}$ and hence HO* are generated more readily. If the reaction is carried out in water with benzene being dispersed in fine droplets through intense stirring, a black precipitate is produced in large quantity which does not dissolve appreciably in common organic solvents and therefore is considered to be polymeric.

EXAMPLE 5

It is clear from the above examples that both US radiation and electrochemical generation of $Fe^{2+}$ facilitate HO* generation and enhance phenol yield. The problems associated with the electrochemical approach are overcome through the simultaneous use of US radiation, which provides a further option for reaction control. Table 4 shows the results of phenol synthesis through combined input of electrochemical and ultrasonic energies. The speed of the reaction and thus the yield at various reaction times depend mainly upon the extent of iron dissolution and solution acidity. Iron dissolution is promoted by the increase in the concentration of water and acid. But acidity increase drives the intermediate back to the starting material as discussed above and is detrimental to the yield. Because of such interplay, a compromise concentration is required. A relatively high concentration of acid (entry 1 of Table 4) slows down the phenol synthesis reaction and reduces the yield. After reaction for 90 min, the yield was less than 15%. By decreasing acid concentration and increasing water concentration, the reaction is accelerated considerably. A yield of 16.5% was reached after 20 min reaction when the amount of sulphuric acid was reduced to 6 mmol (entry 2). Note however that the intensified reaction conditions also destroy phenol synthesised. Rather than increasing with further reaction, the yield is reduced to 11.3% in the subsequent 10 min, indicating that the milder conditions are preferred. Using 1 mmol sulphuric acid at the inception of the reaction without addition of extra water, a reasonably high yield of 12.5% was reached after 30 min of reaction (entry 3), which increased slightly (by ca. 1%) with reaction time (from 30 to 60 min). A significant increase (over 6%) was observed during further reaction (from 60 to 90 min) if water and acid are added (1 mol $H_2SO_4$ and 10 ml $H_2O$ at 60 min reaction). During the reaction of entry 3, the colour of the mixture changed from clear to orange and to reddish-brown, but did not blacken. The reaction was well under control throughout and no precipitate was produced.

The results in Table 4 indicate that significantly higher yield is obtained through the combined input of electrochemical and ultrasonic energies compared with the case of chemical synthesis, chemical synthesis assisted by ultrasonic radiation or unassisted electrochemical synthesis. Finally, it is important to distinguish between phenol yield and the effectiveness of hydroxyl radical generation. Increases in phenol yield indicate improvement in the generation of hydroxyl radicals, but the reverse is not necessarily true. For example, the reduction of phenol yield with increase in acid concentration is due to the adverse effect of acid on the intermediate, rather than deterioration in radical generation. In fact, increases in acid concentration within a certain limit facilitate iron dissolution and thus generation of hydroxyl radicals. Consequently, HO* can be utilised more effectively in other synthetic mineralisation (degradation) reactions, particularly those favoured by strongly acidic conditions.

Because the Fenton's reaction involves strongly oxidising hydrogen peroxide, transpassive dissolution at relatively high potentials was examined as well as active dissolution at low potentials. It was found that in 'dry' acetonitrile (water content <0.02% or 200 ppm), passivation, due to an air-formed film, is maintained for a wide range of potentials up to 0.50 V, well above the corrosion potential $E_{corr} \approx -0.4$ V. Transpassive dissolution at higher potentials is normally controlled by interfacial reactions rather than diffusion in the solution. Addition of a relatively small amount of water (0.5% or 0.28 M) to acetonitrile initiates active dissolution on iron surfaces damaged by previous transpassive dissolution. At a level of 2% water (1.1 M) active dissolution is initiated on undamaged surfaces and proceeds relatively slowly under control by interfacial reactions. Transpassive dissolution at similar potentials meanwhile becomes diffusion-controlled. As water content is increased further (e.g. to 6% or 3.3 M) the electrochemistry of iron becomes progressively similar to that in aqueous solutions, with both active dissolution and passivation being enhanced. Passivation is promoted by addition of hydrogen peroxide as a passivator, but the dynamic balance between the two processes can be shifted to dissolution by increasing solution acidity. The effects of water on the kinetics of iron dissolution and passivation are attributed to the dominant reactivity associated with acidic hydrogen. Based on the potentiostatic and potentiodynamic features, the mechanism of phase change during dissolution can be described in terms of a model of a shifting oxide film formed through two-dimensional nucleation and growth.

EXAMPLE 6

Carbon-carbon bond formation is very important in organic synthesis. One way of forming such a bond is the reaction between two carbon radicals formed when a hydrogen atom of the substrate is abstracted by an hydroxyl radical. Utilising this approach, tetramethyl adipic acid (TMAA) was synthesised from pivalic acid (PA):

$$CH_3C(CH_3)_2COOH + HO^* \rightarrow {}^*CH_2C(CH_3)_2COOH$$

TMAA has the same main carbon chain as adipic acid, one of the starting materials for polyamide fibre polymers, and may be used as a monomer in the production of technologically superior nylon polymers. The additional methyl groups modify the intermolecular interaction of the polymer chains and hence the physical properties such as crystallinity and mechanical properties. Their close proximity to the carbonyl group may exert significant effects on the ester or amide moieties in the polymer and alter the chemical properties such as resistance to hydrolytic, thermal and photo decomposition.

In the experiments, the product in the mixture, identified by thin layer chromatography (TLC) in comparison with a standard and from melting point and spectroscopic data, was separated from unreacted starting material by steam distillation and then extracted into ethyl acetate. Evaporation of the solvent lead to virtually pure TMMA (33% yield based on conversion and 90% yield based on recovered starting material local laboratory conditions. Experiments showed that the conversion rate and yield were influenced by reaction parameters including solution acidity, temperature, concentration of reactants, and the amount of energy input. Under suitable conditions, a conversion rate of over 30% was reached.

Embodiments of the invention have shown that input of ultrasound radiation into the supported-catalyst scheme enhances HO* generation at moderate temperatures (e.g. 30° C.) and hence phenol yield (10–15%), but the catalyst's reusability is poor. Electrochemical dissolution of metallic iron produces pristine ferrous iron and generates hydroxyl radicals more effectively. Phenol yield achieved with this unassisted electrochemical method, however, is moderate (10–13%) due to the solution acidity required and the amounts of iron ions produced, both of which are detrimental. Joint input of ultrasound and electrochemical energies afford further options for reaction control and conditions can be selected which enhance HO* generation yet minimise unwanted further reactions of the product phenol. The combined electrochemical and ultrasound approach presents improved phenol yield of 15–20%, which is about ten-fold higher than reported for a recent chemical method [10].

EXAMPLE 7

In this example, 2-Amino-4-nitrophenol sodium salt (0.15%; 12 mL), sulphuric acid (1M; 12 mL) and 30 wt % hydrogen peroxide (6 mL) were placed in a tall 100 mL beaker in a sonochemical bath (600W 20 khz). Clean iron foil (1 mm×20 mm×100 mm) and clean copper foil (1 mm×20 mm×100 mm) were connected to a DC power generator and immersed into the stirred reaction solution. A current of 1A was applied augmented by sonication with 50% pulsing. After a delay of about 20 seconds gas bubbles appeared and then there was a sudden rush of gas evolution and a rapid temperature rise. The dark brown liquid frothed, boiled and then subsided to a clear straw-coloured liquid. Addition of a slight excess of sodium hydroxide solution (1M) precipitated the hydrated ferric oxide to yield a colourless liquid purged of 2-amino-4-nitrophenol.

Remediation of pollutants, particularly recalcitrant pollutants, forms another aspect of the invention. Pollutants such as dioxins, dyestuffs, polychlorinated biphenyls (PCBs), chlorophenols, and RDX etc can be degraded/mineralised by our method. Dyestuffs are especially good candidates for remediation be the method as the progress of the reaction can be monitored by observing the removal of colour as the degradation proceeds.

Remediation of waste-waters by degradation of the 4-chlorophenol contaminant [16] and RDX contaminated water and soil [25] can be achieved by Fenton-Oxidation methods. RDX (hexahydro-1,3,5-trinitro-1,3,5-triazine), for example, is mobile in soil and recalcitrant at high concentrations [28]. Conventional treatment using incineration to reduce environmental hazards is costly and can provoke strong public opposition. Fenton-type oxidative processes can be used to destroy heterocyclic nitramines and a variety of nitroaromatic residues in water and soil in a manner that is contended to be more-effective, less destructive of soil and, additionally, avoids public dissatisfaction with incineration [28].

In the embodiment described here for mineralisation and remediation purposes it is evident that hydroxyl radical formation and subsequent non-specific oxidation of the organic contaminant is purposefully pursued. The object is to create sufficiently intense conditions where the population density of oxidative radicals indiscriminately attacks and disassembles the otherwise recalcitrant organic contaminants. Contrary to the synthesis conditions imposing deliberate restraint by setting the mildest parameters consistent with reaction rate and product yield, the consideration now is acceleration of the enhanced Fenton process beyond an energy threshold where destruction of organic structures predominates.

With dyestuff molecules, for example, that threshold can be observed when rapid discharge of colour intensity occurs. Thus, for example, picramate dyestuffs and their process intermediates are not readily degraded by hydrogen peroxide alone, nor by traditional Fenton chemistry. We have now found that highly coloured dyestuff waste containing picramates are made tractable to mineralisation under conditions where acid and hydrogen peroxide concentrations are relatively high and iron or copper ions separately or in combination are produced in situ. Typical reactants as well as picramates that respond to this degradation attack include nitrophenols, picric acid and azo dyestuffs. In these instances discharge of colour is accompanied by active corrosion of the metal(s) used. Iron and copper for example singly or in combination rapidly corrode and dissolve in the oxidative mixture. A feature of the reaction is the sudden exotherm with effervescence which results in a drastic decrease in colour. The effect has the characteristics of a branched-chain reaction which proceeds via a relatively. quiescent initiating period then rapidly accelerates as the chain-branching process gains in vigour. In the mineralising reaction conditions a spate of hydroxyl radicals forms to fragment dyestuff substrates and their residues.

Electrochemical, ultrasonic, photolytic and thermal energies singly or in any combination can augment the remediation process. Their participation provides a choice of factors that can affect the time to initiate the surge in reaction rate and ameliorate process costs such as lowering the relative concentrations of hydrogen peroxide and/or acid in the reaction mixture. Through the setting of such rate-enhancing conditions the destructive energy threshold usually occurs within a few minutes and effective degradation of organic residues follows almost immediately. This compares with Fenton reaction conditions below the energy threshold which may not bring about appreciable degradation of a particularly stable organic contaminant after 12 or more hours.

Modifications and improvements can be incorporated without departing from the scope of the invention.

References

1. E. Brillas, R. M. Bastida, E. Llosa and J. Casado, *J. Electrochem. Soc.*, 142 (1995) 1733.
2. E. Brillas, E. Mur and J. Casado, *J. Electrochem. Soc.*, 143 (1996) L49.
3. F. Trabelsi, H. Ait-Lyazidi, B. Ratsimba, A. M. Wilhelm, H. Delmas, P.-L. Fabre and J. Berlan, *Chem. Eng. Sci.*, 51 (1996) 1857.
4. D. D. Coffman, E. L. Jenner and R. D. Lipscomb, *J. Am. Chem. Soc.*, 80 (1958) 2864.
5. D. H. Bremner, S. R. Mitchell and H. Staines, *Ultrason. Sonochem.*, 3 (1996) 47.
6. C. Walling and R. A. Johnson, *J. Am. Chem. Soc.*, 97 (1975) 363.
7. M. A. Oturan and J. Pinson, *J. Phys. Chem.*, 99 (1995) 13948.
8. N. V. Raghavan and S. Steenken, *J. Am. Chem. Soc.*, 102 (1980) 3495.
9. C. Walling, *Acc. Chem. Res.*, 8 (1975) 125.
10. T. Tagawa, Y.-J Seo and S. Goto, *J. Mol. Cat.*, 78 (1993) 201.
11. T. Tzedakis, A. Savall and M. J. Clifton, *J. Appl. Electrochem.*, 19 (1989) 911.
12. *Encyclopedia of Chemical Technology*, Ed. I. Kroschwitz, John Wiley & Sons, New York, 1996, Vol, 18, p592.
13. R. Tomat -and E. Vecchi, *J. Appl. Electrochem.*, 1 (1971) 185.
14. R. Tomat, R. Salmaso and S. Zecchin, *Electrochim. Acta*, 39 (1994) 2475.

15. A. Kunai, S. Hata, S. Ito and K. Sasaki, *J. Am. Chem. Soc.*, 108 (1986) 6012.
16. E. Brillas, R. Sauleda and J. Casado, *J. Electrochem. Soc.*, 145 (1998) 759.
17. T.J. Mason, *Advances in Sonochemistry*, Vols. 1 and 2, JPI press, London UK (1990 and 1991).
18. K. S. Suslick, D. A. Hammerton and R. E. Cline Jr., *J. Am. Chem. Soc.*, 108 (1986) 5641.
19. D. J. Walton and S. S. Phull, *Adv. Sonochem.*, 4 (1996) 205.
20. R. G. Compton, F. Marken, C. H. Goeting, R. A. J. McKeown, J. S. Foord, G. Scarsbrook, R. S. Sussmann and A. J. Whitehead, *Chem. Commun.*, (1998) 1961.
21. I. Z. Shirgaonkar and A. B. Pandit, *Ultrason. Sonochem.*, 5 (1998) 53.
22. G. Wranglen, *An Introduction to Corrosion of Metals*, Chapman & Hall, London, 1985.
23. M. Keddam, in *Corrosion Mechanisms in Theory and Practice*, edited by P. Marcus and J. Ouder, Marcel Dekker, New York, 1995. Ch.3, p.55.
24. E. Heitz, in *Advances in Corrosion Science and Technology*, edited by M. G. Fontana and W. Staehle, Plenum Press, New York, 1974, p.149.
25. R. G. Kelly and P. J. Moran, *Corros. Sci.* 30 (1990) 495.
26. F.-B. Li, D. H. Bremner and A. E. Burgess, *Corros. Sci.*, 1999, in the press.
27. J. Feng, L. L. Houk, D. C. Johnson, S. N. Lowery and J. J. Carey, *J. Electrochem. Soc.*, 142 (1995) 3626.
28. E. L. Bier et al, *Environmental Toxicology and Chemistry*, 18 (1999) 1078.

TABLE 1

Phenol yields from chemical synthesis using ultrasonic probe.

| | Reaction time/min | | | US level & duration | Composition of starting mixture |
|---|---|---|---|---|---|
| No | 30 | 60 | T/° C. | | |
| 1 | 2.7 | 2.2 | 35 ± 5 | 3, 100% | $C_6H_6$ 2.2M, $H_2O_2$ 0.73M |
| 2 | 2.3 | 1.7 | 35 ± 5 | 5, 100% | As no. 1 |
| 3 | 1.8 | 1.6 | 0–5 | 3, 100% | As no. 1 |

TABLE 2

Phenol yields from chemical synthesis using cup-horn ultrasonic bath*.

| | Reaction time/min | | | | US level & duration | Composition of starting mixture |
|---|---|---|---|---|---|---|
| No | 10 | 60 | 60 | 90 | T/° C. | |
| 1 | 0.4 | 1.7 | 2.8 | — | 35 ± 5 | 5, 20% | $C_6H_6$ 2.2M, $H_2O_2$ 0.73M |
| 2 | — | 3.0 | 6.2 | 7.0 | 35 ± 5 | 5, 50% | As no. 1 |
| 3 | — | 12.4 | 13.0 | — | 35 ± 5 | 8, 50% | $C_6H_6:H_2O_2 = 1:2$ |
| 4 | — | 0.0 | 0.0 | — | 35 ± 5 | 8, 50% | As no. 3, + 6 mmol + 6 mmol $H_2SO_4$ |
| 5 | — | 9.1 | 8.9 | — | 65 ± 5 | 8, 50% | $C_6H_6:H_2O_2 = 1:1.25$ |
| 6 | 15.3 | 14.5 | — | — | 65 ± 5 | 8, 50% | $C_6H_6:H_2O_2 = 1:1.29$ |

*The '—' signs in table indicate that phenol yields were not determined because the reaction was either insignificant at short times (eg entry 1) or had completed at long times (eg entry 6) under the given conditions. This is also the case for Tables 3 and 4 below.

TABLE 3

Phenol yields from electrochemical synthesis.

| | Reaction time/min | | | | | Current/ | Composition of |
|---|---|---|---|---|---|---|---|
| No | 20 | 25 | 110 | 180 | T/° C. | mA | starting mixture |
| 1 | — | — | 9.0 | — | 22 ± 5 | 25 ± 5 | $C_6H_6$ 1M, $C_6H_6:H_2O_2 = 1:1$, 1 mmol $H_2SO_4$ |
| 2 | — | — | — | 2.8 | 22 ± 5 | 25 ± 5 | As no. 1, but 6 mmol |
| 3 | 10.6 | — | — | — | 22 ± 5 | 25 ± 5 | $H_2SO_4$ |
| 4 | 11.7 | 13.0 | — | — | 22 ± 5 | 25 ± 5 | As no 1, + 0.5 mmol HCl $C_6H_6:H_2O_2 = 1:2$, 6 mmol $H_2SO_4$ + 20 l $H_2O$ |

TABLE 4

Phenol yields achieved through combined input of electrochemical and ultrasonic energies.

| | Reaction time/min | | | | | | US level and duration | Composition of starting mixture |
|---|---|---|---|---|---|---|---|---|
| No | 20 | 30 | 40 | 60 | 90 | T/° C. | | |
| 1 | — | — | 2.3 | 7.1 | 14.6 | 35 ± 5 | 8, 50% | $C_6H_6$ 1M, $H_2O_2$ 2M, 6 mmol $H_2SO_4$.[a] |
| 2 | 16.5 | 11.3 | — | — | — | 35 ± 5 | 8, 50% | As no 1, + 10 ml $H_2O$ |
| 3 | — | 12.5 | — | 13.4 | 19.5 | 35 ± 5 | 8, 50% | As no 1, but 1 mmol $H_2SO_4$.[b] |

[a] At reaction times of 20 and 40 min, 15 ml $H_2O$ and 12 mmol $H_2SO_4$ were added in two portions.
[b] At 60 min of reaction, 10 ml $H_2O$ and 1 mol $H_2SO_4$ were added.

What is claimed is:

1. A method of reacting chemicals, the method comprising:
   generating $M^{n+}$ ions through electrochemical dissolution of at least one metal electrode in an electrolyte wherein n is any value from 1 to 7;
   exposing said $M^{n+}$ ions to $H_2O_2$ to generate HO* radicals; and
   chemically reacting the HO* radicals with one or more reactants to form reaction products
   wherein the at least one metal electrode is exposed to ultrasound energy.

2. The method as claimed in claim 1, wherein the at least one metal electrode is exposed to electrochemical energy.

3. The method as claimed in claim 1 wherein there are two electrodes.

4. The method as claimed in claim 1, wherein the at least one metal electrode comprises iron.

5. The method as claimed in claim 4 wherein the step of generating $M^{n+}$ ions through electrochemical dissolution of the at least one metal electrode in an electrolyte comprises generating $Fe^{2+}$ ions and the $Fe^{2+}$ ions react with the $H_2O_2$ before reaching solvation.

6. The method as claimed in claim 1, wherein the at least one metal electrode comprises at least one metal selected from the group consisting of iron, cobalt, copper, cerium, nickel, stainless steel, manganese, vanadium, molybdenum, titanium, platinum, iridium, osmium, ruthenium, gold and silver.

7. The method as claimed in claim 1, wherein the at least one metal electrode comprises a first electrode comprising $Fe^{2+}/Fe^{3+}$ in conjunction with $Ce^{3+}/Ce^{4+}$ and a second electrode comprising a noble metal electrode, and wherein the following reaction takes place at the first electrode:

$$Fe^{3+}+Ce^{3+} \rightarrow Fe^{2+}+Ce^{4+}.$$

8. The method as claimed in claim 1, wherein the chemical reaction comprises chemical decomposition.

9. The method as claimed in claim 1, wherein the chemical reaction comprises the synthesis of chemicals.

10. The method as claimed in claim 1, wherein the HO* radicals are utilised in a hydroxylation reaction.

11. The method as claimed in claim 1, wherein the method involves the use of catalytic schemes and electrochemical regeneration of $M^{n+}$ ions, and wherein M is Fe or another metal and n is any value from 1 to 7.

12. The method as claimed in claim 11 wherein the $M^{n+}$ is $Fe^{2+}$ and is electrochemically regenerated according to the equation below $$Fe+2Fe^{3+} \rightarrow 3Fe^{2+}.$$

13. The method as claimed in claim 1, wherein the step of exposing said $M^{n+}$ ions to $H_2O_2$ to generate HO* radicals proceeds according to the equation $M^{n+}+H_2O_2 \rightarrow HO*+HO^-+M^{(n+1)+}$, wherein M is Fe or another metal and n is any value from 1 to 7.

14. The method as claimed in claim 1, wherein the one or more reactants are carbon based reactants and the HO* radicals with the carbon-based reactants to remove a hydrogen atoms and generate a carbon-based radicals.

15. The method as claimed in claim 14, wherein the carbon-based radicals can then dimerize or react with other carbon-based radicals or other reactants.

16. The method as claimed in claim 1, wherein the at least one metal electrode comprises an anode and cathode immersed in the electrolyte to form a cell.

17. The method as claimed in claim 16, further comprising the step of applying an external electrical current to the cell.

18. The method as claimed in claim 16, wherein a miscible unreactive solvent and water mixture is used as the electrolyte.

19. The method as claimed in claim 18, wherein the miscible unreactive solvent comprises at least one solvent selected from the group consisting of acetonitrile, tetrahydrofuran, dioxin, dimethyl formamide and dimethyl sulphoxide.

* * * * *